US008415131B2

(12) United States Patent
Wang et al.

(10) Patent No.: US 8,415,131 B2
(45) Date of Patent: Apr. 9, 2013

(54) M13 BACTERIOPHAGE AS A CHEMOADDRESSABLE NANOPARTICLE FOR BIOLOGICAL AND MEDICAL APPLICATIONS

(75) Inventors: Qian Wang, Columbia, SC (US); Kai Li, Henan (CN); Charlene Mello, Rochester, MA (US)

(73) Assignee: University of South Carolina, Columbia, SC (US)

( * ) Notice: Subject to any disclaimer, the term of this patent is extended or adjusted under 35 U.S.C. 154(b) by 560 days.

(21) Appl. No.: 12/604,575

(22) Filed: Oct. 23, 2009

(65) Prior Publication Data
US 2010/0190233 A1 Jul. 29, 2010

Related U.S. Application Data

(60) Provisional application No. 61/197,269, filed on Oct. 23, 2008.

(51) Int. Cl.
*C12Q 1/70* (2006.01)
*C12N 7/00* (2006.01)
*C12N 7/06* (2006.01)
*C07C 245/00* (2006.01)
*C07D 249/16* (2006.01)

(52) U.S. Cl. ......... 435/235.1; 435/5; 435/238; 436/802; 534/558; 548/257

(58) Field of Classification Search ............... None
See application file for complete search history.

(56) References Cited

U.S. PATENT DOCUMENTS

| 6,350,574 | B1 * | 2/2002 | Montelaro et al. | ............. | 435/5 |
| 6,933,109 | B2 * | 8/2005 | Anderson | .................. | 435/5 |
| 2007/0224695 | A1 | 9/2007 | Wang et al. | | |

OTHER PUBLICATIONS

Bar, et al., "Killing Cancer Cells by Targeted Drug-carrying Phage Nanomedicines", *BMC Biotechnology*, 2008, 8, 1-14.
Khor, et al.,"Novel Strategy for Inhibiting Viral Entry by Use of a Cellular Receptor-Plant Virus", Chimera *J. Virol*. 2002, 76, 4412-4419.
Larocca, et al., "Receptor-mediated gene transfer by phage-display vectors: applications in functional genomics and gene therapy", *Drug. Discov. Today*. 2001, 6, 793-801.
Lee, et al., "Adaptations of Nanoscale Viruses and Other Protein Cages for Medical Applications", *Nanomedicine 2*, 2006, 137-149.
Lee, et al., "Cobalt Ion mediated Self-Assembly of Genetically Engineered Bacteriophage for Biomimetic Co-Pt Hybrid Material" *Biomacromolecules*, 2006, 7, 14-17.
Mao, et al., "Virus-based Toolkit for the Directed Synthesis of Magnetic and Semiconducting Nanowires", *Science*, 2004, 303, 213-217.

(Continued)

*Primary Examiner* — Zachariah Lucas
*Assistant Examiner* — Stuart W Snyder
(74) *Attorney, Agent, or Firm* — Dority & Manning, P.A.

(57) ABSTRACT

Reactive and modified M13 bacteriophages, and methods of making and using the same, are generally provided. The reactive M13 bacteriophage can include a alkyne functional group covalently attached to the M13 bacteriophage. The modified M13 bacteriophage can include a substituent covalently attached to the M13 bacteriophage via a 1,2,3-triazole linkage. Dual-modified M13 bacteriophages are also generally provided, and can include a cancer-targeting substituent covalently attached to the M13 bacteriophage and a fluorescent group covalently attached to the M13 bacteriophage. The modified M13 bacteriophages can not only be employed as a fluorescent probe for cancer imaging, but also can be used as biomaterials for cell alignment and scaffolding.

4 Claims, 6 Drawing Sheets

OTHER PUBLICATIONS

Nam, et al., "Virus-Enabled Synthesis and Assembly of Nanowires for Lithium Ion Battery Electrodes", *Science*, 2006, 312, 885-888.

Rae, et al., "Systemic trafficking of plant virus nanoparticles in mice via the oral route", *Virology*, 2005, 343, 224-235.

Singh, et al., "Viruses and Their Uses in Nanotechnology", *Drug Dev. Res.* 2006, 67, 23-41.

Shenton, et al., "Inorganic-Organic Nanotube Composites from Template Mineralization of Tobacco Mosaic Virus", *Mann, Adv. Mater.* 1999, 11, 253-256.

Singh, et al., "Canine parvovirus-like particles, a novel nanomaterial for tumor targeting", *Journal of Nanobiotechnology*, 2006, 4:2.

Massaro, J. M. E. R, *Humana Press*, 2002, 376.

Rijnboutt, et al., "Endocytosis of GPI-linked Membrane Folate Recepotr-α" *J. Cell. Biol.* 1996, 132, 35-47.

Rostovtsev, et al., "A Stepwise Huisgen Cycloaddition Process: Copper(I)—Catalyzed Regioselective "Ligation" of Azides and Terminal Alkynes", *Angew. Chem.* 2002, 114, 2708-2711; *Angew. Chem. Int Ed.* 2002, 41, 2596-2599.

\* cited by examiner

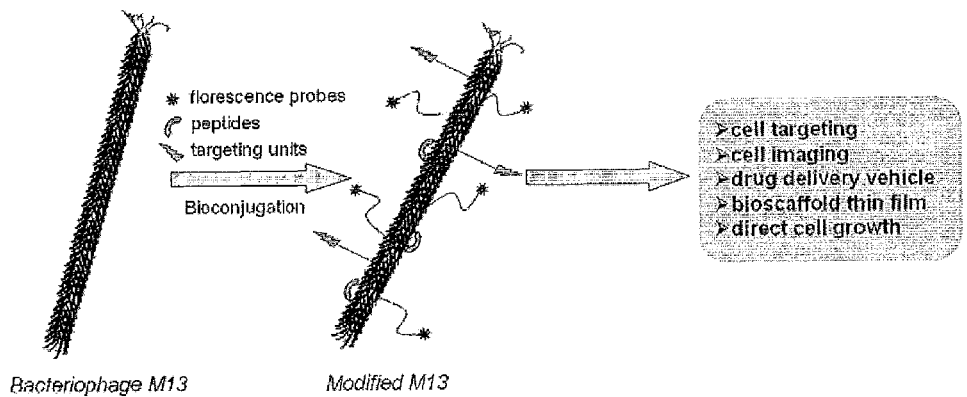
FIG. 1
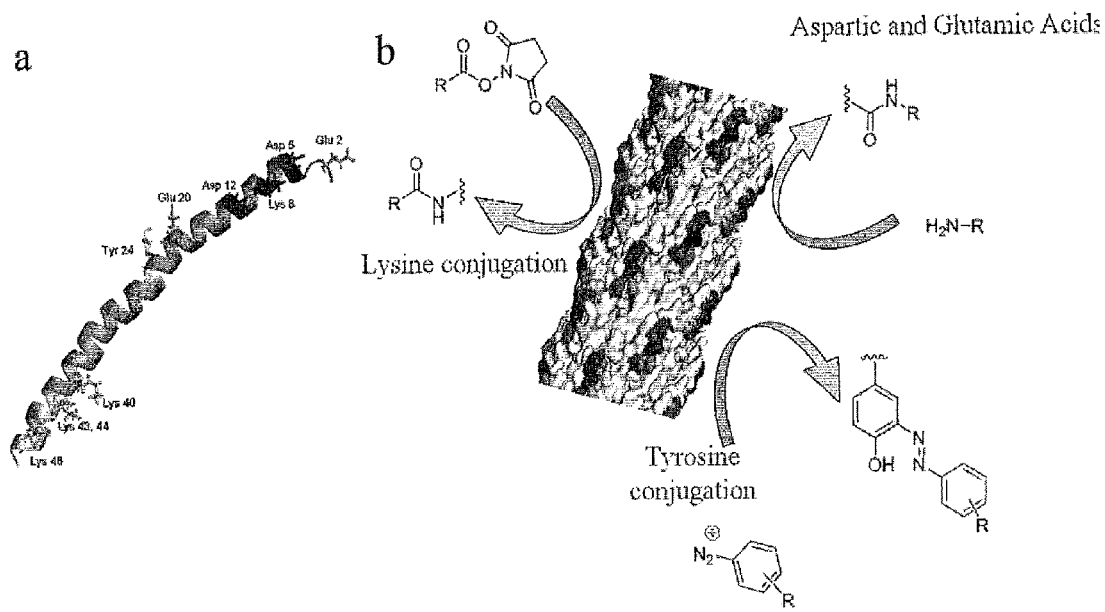
FIG. 2A   FIG. 2B

M13 BACTERIOPHAGE AS A CHEMOADDRESSABLE NANOPARTICLE FOR BIOLOGICAL AND MEDICAL APPLICATIONS

PRIORITY INFORMATION

The present application claims priority to U.S. Provisional Patent Application Ser. No. 61/197,269 filed on Oct. 23, 2008 of Wang, et al. titled "M13 Bacteriophage as a Chemoaddressable Nanoparticle for Biological and Medical Applications," the disclosure of which is incorporated by reference herein.

GOVERNMENT SUPPORT CLAUSE

The present invention was developed with funding from the National Science Foundation under award CHE-0748690 and the U.S. Army Natick Soldier Research, Development and Engineering Center AH52 program. Therefore, the government retains certain rights in this invention.

BACKGROUND

Virus and virus-like particles are being extensively emerged as promising building blocks for biomedical applications. Viruses provide a wide array of shapes as rods and spheres, and variety of sizes spanning from tens to hundreds of nanometers. These protein structures are evolutionary tested, multi-faceted systems with highly ordered spatial arrangement, and natural cell targeting and genetic information storing capabilities.

For example, virus and virus-like particles are being explored for targeting tumors. Currently, the ability to target tumors and deliver therapeutics to specific locations in the body is a primary goal in cancer medicine. Targeted delivery of drugs is ideal in order to enhance therapeutic benefit as well as reduce systemic toxicity.

However, a need exists for further development of compositions and methods for targeting tumor growth, for treating the tumor cells, and expanding their understanding to develop further treatments.

SUMMARY

Objects and advantages of the invention will be set forth in part in the following description, or may be obvious from the description, or may be learned through practice of the invention.

A reactive M13 bacteriophage including an alkyne functional group covalently attached to an M13 bacteriophage is generally provided according to one embodiment of the present invention. The alkyne functional group can be covalently attached to the M13 bacteriophage via an ortho position of a phenyl ring of a tyrosine amino acid. Additionally, the alkyne functional group can be covalently attached to the M13 bacteriophage via the ortho position of the phenyl ring of the tyrosine amino acid via a benzene diazonium linkage, such in the exemplary embodiment shown in the following formula:

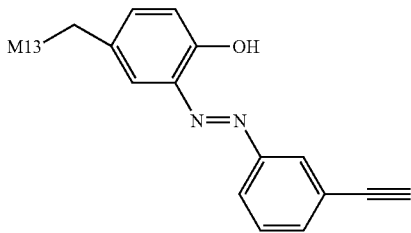

where M13 represents a peptide chain of the M13 bacteriophage. The reactive M13 bacteriophage of claim 1 can further include a fluorescent group, which can be, in one embodiment, covalently attached to the M13 bacteriophage via a terminal amine of an alanine amino acid or a functional amino group of a lysine amino acid.

In another embodiment, the present invention is generally directed to a modified M13 bacteriophage comprising a substituent covalently attached to the M13 bacteriophage via a 1,2,3-triazole linkage. For example, the substituent can be covalently attached to the M13 bacteriophage via a tyrosine amino acid such that the 1,2,3-triazole linkage is covalently attached to the tyrosine amino acid via a benzene diazonium linkage attached at an ortho position of the phenyl ring of the tyrosine amino acid, such as represented by the exemplary structure:

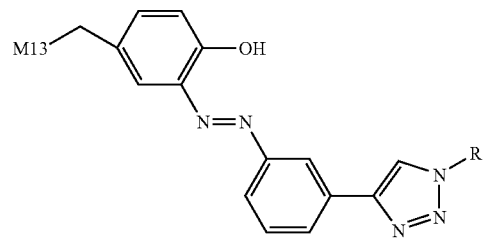

where R represents the substituent and M13 represents a peptide chain of the M13 bacteriophage. A fluorescent group can also be covalently attached to the M13 bacteriophage via a terminal amine of an alanine amino acid or a functional amino group of a lysine amino acid.

A dual-modified M13 bacteriophage is generally provided according to yet another embodiment of the present invention. The dual-modified M13 bacteriophage includes a cancer-targeting substituent covalently attached to the M13 bacteriophage and a fluorescent group covalently attached to the M13 bacteriophage. For example, the cancer-targeting substituent can be covalently attached to the M13 bacteriophage via a terminal amine of an alanine amino acid or a functional amino group of a lysine amino acid. Also, the fluorescent group can be covalently attached to the M13 bacteriophage via a carboxyl group on the M13 bacteriophage.

Methods of modifying a M13 bacteriophage are also generally provided.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which:

FIG. 1 shows a schematic illustration of conjugation of small molecules onto the surface of a M13 bacteriophage and their potential applications.

FIG. 2 shows a) a single subunit structure of coat protein P8 is presented as ribbon diagram with possible reactive amino acids being highlighted and b) helical organization of M13 major coat proteins P8 and possible bioconjugation reactions.

Figure 3:
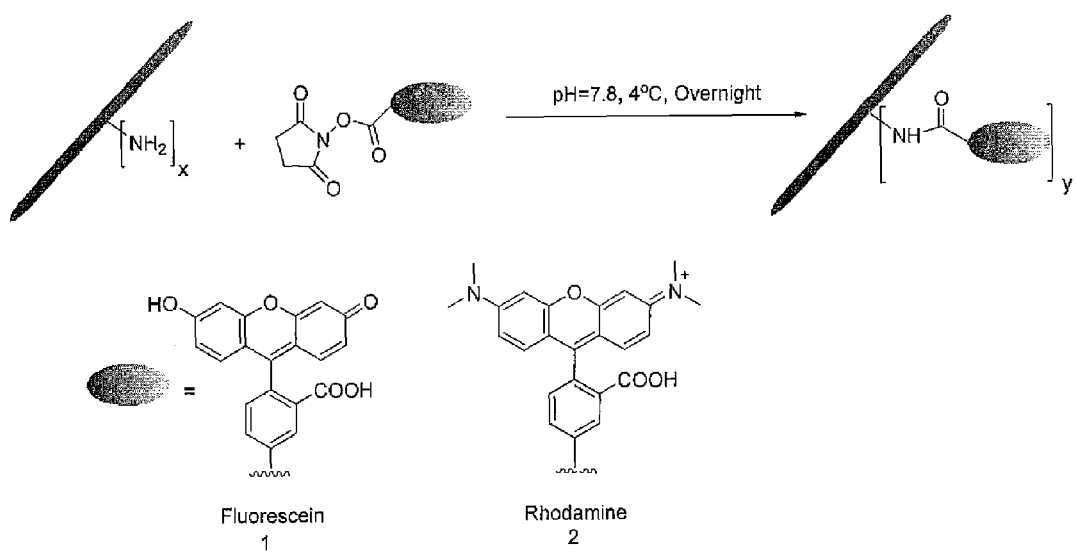
FIG. 3 shows bioconjugation of lysine residues of M13 with exemplary florescence dyes (1) fluorescein-NHS and (2) TMRD-NHS.
Figure 4:
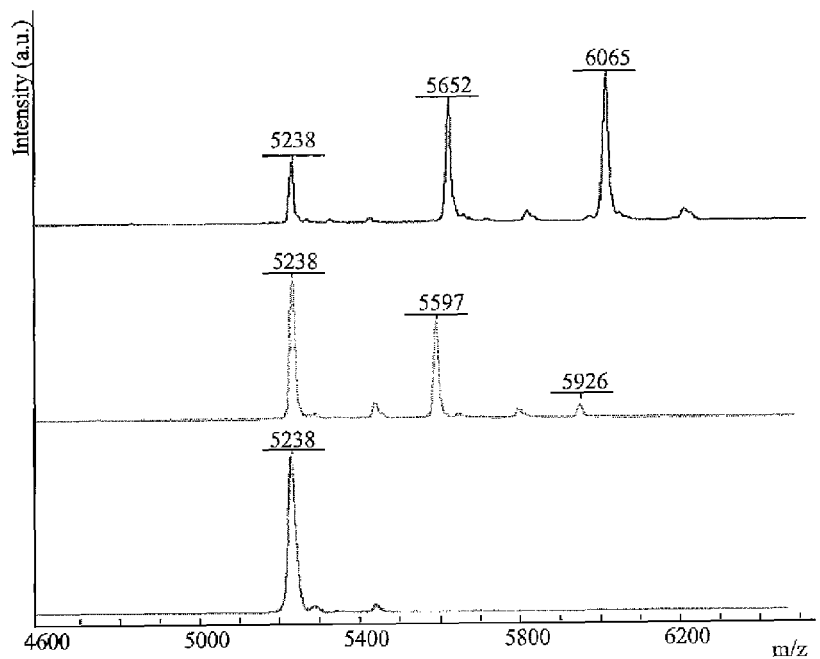
FIG. 4 shows MALDI-TOF MS of the coat protein P8 of unmodified M13 (bottom line), fluorescein modified M13 (middle line) and TMRD modified M13 (top line).
Figure 5:
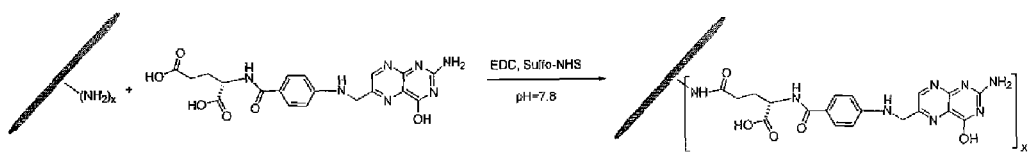
FIG. 5 shows a reaction for conjugating folic acid onto the surface of M13 bacteriophage.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Generally speaking, the present disclosure is directed to reactive and modified M13 bacteriophages along with their use for cell targeting, cell imaging, drug delivery vehicle and bio-scaffold which can direct cell growth. The multivalent M13 bacteriophage can be modified with different chemical compounds and functional groups (i.e., "substituents"), such as bio-imaging agents (fluorescent dyes, magnetic contrast imaging agents, etc.), cell targeting molecules (boronic acids, folic acid, antibodies, etc.), and drugs or other pharmaceutical agents at high local concentrations to increase detection sensitivity and efficacy for therapeutic applications. The combination of these multiple derivatizations on the nanoparticles could yield versatile units with specific cell-targeting for drug/gene delivery, with simultaneous in-vivo imaging for biomedical purposes. Furthermore, M13 can be easily fabricated into liquid-crystal like thin films either by slow drawing or withdrawing method which can direct various mammalian cells growth in a well defined direction. Thus, the chemical modification of M13 bacteriophage can be particularly applicable to tumor cell targeting, cell imaging, drug delivery, and/or fabrication of M13 thin film and directing cell growth.

I. M13 Bacteriophage

M13 is a filamentous bacteriophage composed of circular, single-stranded DNA (ssDNA), which is 6407 nucleotides long encapsulated by approximately 2700 copies of the major coat protein P8, and capped with 5 copies of four different minor coat proteins (P9, P7 P6, and P3) on the ends. The major coat protein is primarily assembled from a 50 amino acid called pVIII (or P8), which is encoded by gene VIII (or G8) in the phage genome. For a wild type M13 particle, it takes approximately 2700 copies of P8 to make the coat about 880 nm long. The diameter of M13 is about 6.6 nm. The coat's dimensions are flexible and the number of P8 copies adjusts to accommodate the size of the single stranded genome it packages. As shown in FIG. 1, crystal structure of M13 clearly shows that multiple reaction amino acids are exposed on the outer surface of M13 which can be modified by traditional bioconjugation methods.

M13 bacteriophage is an excellent candidate as one of the virus-based nanoparticles due to it has unique size and good stability in a wide range of pH, and suitability for genetic manipulation as well as chemical bioconjugation. Compared to the semiconductor nanocrystal quantum dots and other virus-based nanoparticles, the dye-loaded M13 bacteriophage has many advantages. Firstly, dye-loaded M13 bacteriophage was a water-soluble nanoparticle with small hydrodynamic diameter, and most of the semiconductor nanocrystal quantum dots are not water soluble. Secondly, with the unique shape, dye-loaded M13 bacteriophages can get into the cells, giving it potential for development of a new system for targeted drug delivery. Thirdly, with the large dye-carrying capability, M13 bacteriophages display superior brightness and photostability which was better than other virus-based nanoparticles. In addition, the new thin film, made by bacteriophage M13, can be employed as a new scaffold to direct cell growth.

II. Modification of an Amino Group on the M13 Bacteriophage

As shown in FIG. 2A, there are five lysines and one N-terminal amine (e.g., alanine 1 in the shown embodiment) in the P8 coat protein of M13 bacteriophage. However, as shown in FIG. 2B, only ala 1 and lys 8 are exposed on the outer surface and easily accessed, while the other four lysines are buried by other proteins. Compared with lys 8, ala 1 generally has larger solvent accessibility surface due to the crystal structure of the P8 protein, which indicates that the N-terminal amino group of the M13 bacteriophage (i.e., ala 1) is readily available for conjugation reactions. However, the amine functionality of the lysine amino acid (e.g., lys 8) is also available for conjugation reactions.

For example, a fluorescent group (e.g., 5-(and 6-)carboxyfluorescein, succinimidyl ester) can be covalently attached to the M13 via the N-terminal amino group of an amino acid on the M13 bacteriophage (e.g., ala 1) or the amino functional group on a lysine amino acid on the M13 bacteriophage (e.g., lys 8). Such a reaction relies on the ability of the succinimidyl ester acylate amino groups much more rapidly than they are hydrolyzed by the aqueous solvent.

Other substituents can be covalently attached to the M13 via the amino groups on the M13 bacteriophage. For example, a cancer-targeting substituent (e.g., folic acid) can be covalently attached to the M13 via the N-terminal amino group of an amino acid on the M13 bacteriophage and/or the amino functional group of a lysine amino acid on the M13 bacteriophage. In one particular embodiment, for instance, the carboxylic acid group of folic acid can be activated (e.g., through reaction with 1-ethyl-3-(3-dimethylaminopropyl) carbodiimide (EDC) and N-hydroxysulfosuccinimide (Sulfo-NHS)), followed by an acylation reaction with the amine group(s) of the M13 bacteriophage.

III. Modification of a Tyrosine Amino Acid on the M13 Bacteriophage

The M13 bacteriophage can also be modified via a tyrosine amino acid on the M13 bacteriophage (e.g., tyr 24 as shown in FIG. 2A). A tyrosine amino acid on the M13 bacteriophage can have the following structure:

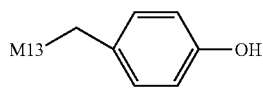

where M13 represents a peptide chain of the M13 bacteriophage.

Modification of the tyrosine amino acid on the M13 bacteriophage involves a two-step reaction. First, an alkyne functional group can be added to the tyrosine amino acid to produce a reactive M13 bacteriophage. In one embodiment, the alkyne functional group can be covalently attached to the M13 bacteriophage via an ortho position of a phenyl ring of a tyrosine amino acid. For example, the alkyne functional group can be covalently attached to the M13 bacteriophage via an ortho position of a phenyl ring of a tyrosine amino acid via a benzene diazonium linkage, such as shown in the following structure:

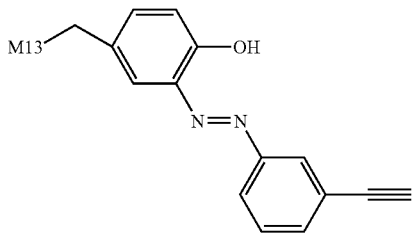

where M13 represents a peptide chain of the M13 bacteriophage.

Figure 9:
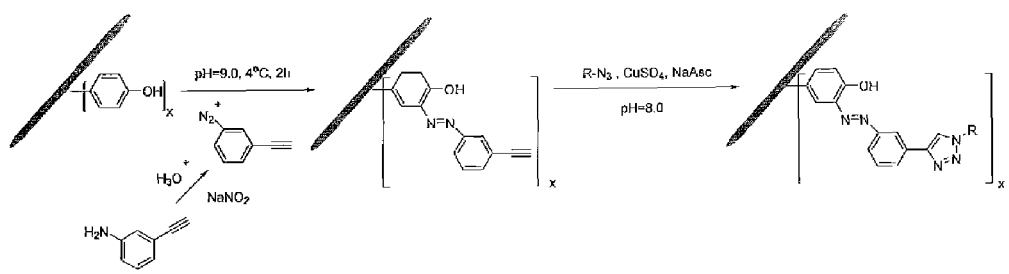
FIG. 9 shows bioconjugation of M13 with RGD motifs.
Figure 10:
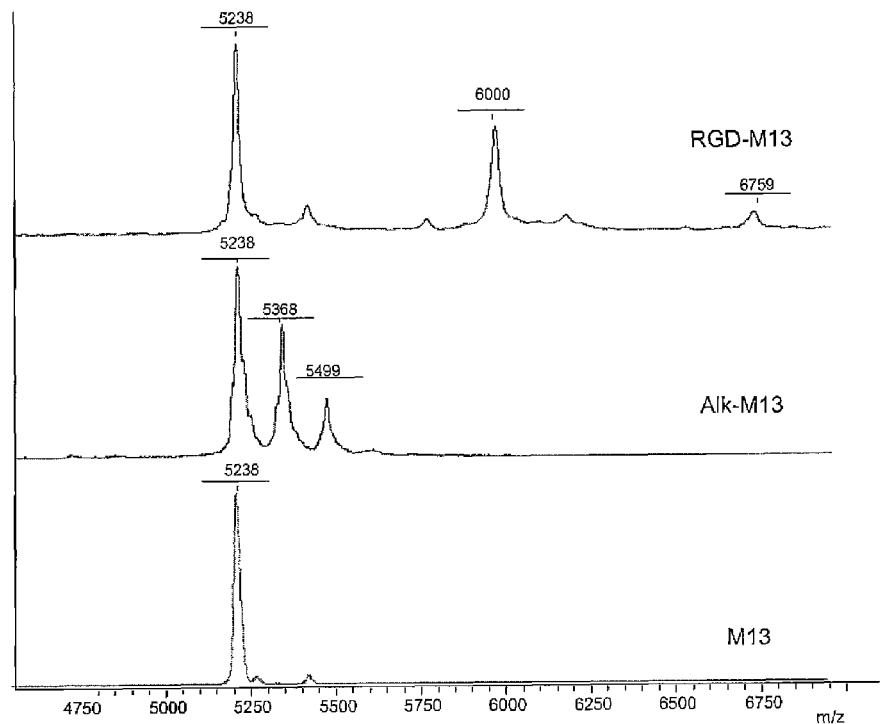
FIG. 10 shows MALDI-TOF MS of the coat protein P8 of unmodified M13 (5,238 m/z) and modified M13.

In order to modify the M13 bacteriophage to include the alkyne functional group covalently attached to the M13 bacteriophage via the ortho position of the phenyl ring of the tyrosine amino acid via the benzene diazonium linkage, as shown above, the tyrosine amino acid of the M13 bacteriophage can be reacted with an N-hydroxyl succinimidyl (BHS) ester-alkyne (NHS-alkyne) to generate the reactive M13 bacteriophage having the alkyne functionality. The first reaction shown in FIG. 9 shows an exemplary reaction to form the reactive M13 bacteriophage having the alkyne functionality covalently attached to the M13 bacteriophage via an ortho position of a phenyl ring of a tyrosine amino acid via a benzene diazonium linkage. However, other linkage compounds having both an alkyne functional group and a primary amino function group in the presence of hydronium ions (i.e., $H_3O^+$) and nitrite ions is $NO_2^-$ to form a HCC-L-$N_2^+$ intermediate, where "L" represents the linkage compound, that is reactive with the ortho-position of the phenyl ring of the tyrosine amino acid to form a diazonium linkage.

An azide substituted substituent can then be reacted with the reactive M13 bacteriophage via this alkyne functional group of the reactive M13 bacteriophage through formation of a 1,2,3-triazole linkage, such as described in U.S. Publication No. 2007/0224695 of Wang, et al., the disclosure of which is incorporated herein by reference. The second reaction shown in FIG. 9 shows such an exemplary reaction of an alkyne functional group with an azide substituted substituent (i.e., R—$N_3$, where R represents the substituent). Such a reaction can be generally referred to as "Azide-Alkyne Huisgen Cycloaddition", where 1,3-dipolar cycloaddition between an azide and a terminal or internal alkyne results in a triazole linkage.

Although this reaction can afford the triazole as a mixture of the 1,4-adduct and the 1,5-adduct, one particular embodiment can utilize a copper(I) catalyzed reaction such that the organic azides and terminal alkynes are united to afford 1,4-regioisomers of 1,2,3-triazoles as sole products (i.e., substitution at positions 1' and 4'). While the copper(I) catalyzed variant gives rise to a triazole from a terminal alkyne and an azide, formally it is not a 1,3-dipolar cycloaddition and thus should not be termed a Huisgen cycloaddition. This reaction is better termed the Copper(I)-catalyzed Azide-Alkyne Cycloaddition ("CuAAC").

For example, a substituent can be covalently attached to the M13 bacteriophage via a tyrosine amino acid, where the 1,2,3-triazole linkage is covalently attached the tyrosine amino acid via a benzene diazonium linkage attached at an ortho position of a phenyl ring of the tyrosine amino acid, such as shown according to the exemplary structure below:

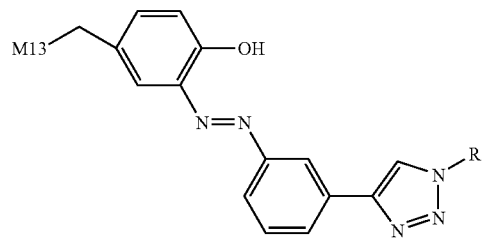

where R represents the substituent and M13 represents a peptide chain of the M13 bacteriophage. Thus, a modified M13 bacteriophage having a substituent ("R") covalently attached thereto via a 1,2,3-triazole linkage (and, optionally, a benzene diazonium linkage, as shown) can be generally formed.

IV. Modification of Carboxyl Groups on the M13 Bacteriophage

Figure 7:
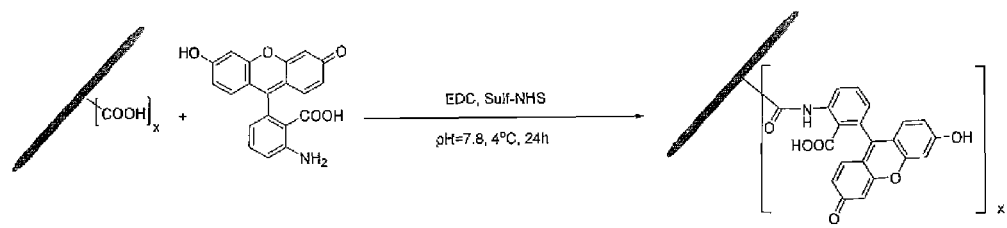
FIG. 7 shows the bioconjugation of lysine residues of M13 with fluoresceinamine.
Figure 8:
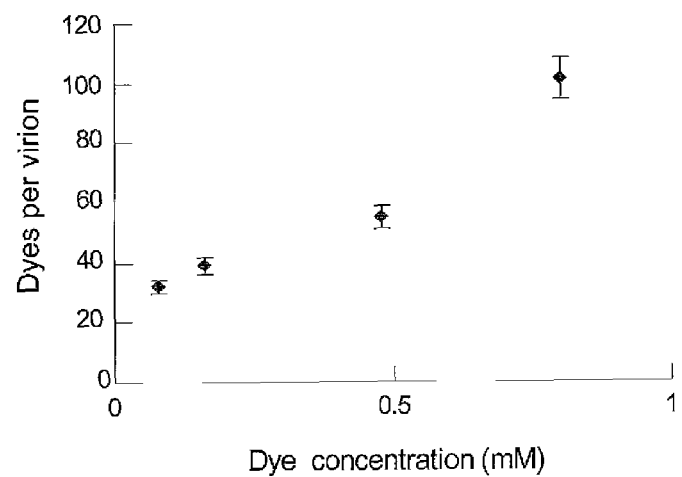
FIG. 8 shows the loading of fluorescein on M13 bacteriophage related to the concentration of dye molecules.

Carboxyl groups on the M13 bacteriophage can also be utilized to add substituents. For example, fluorescent groups can be covalently attached to the M13 bacteriophage via the carboxyl groups such as shown in FIG. 7. In one embodiment, for instance, water soluble carbodiimides 1-ethyl-3-(3-dimethylaminopropyl) carbodiimide (EDC) and N-hydroxysulfosuccinimide (Sulfo-NHS) can be used to activate carboxylate acid residues on the bacteriophage surface to form esters, which can then be reacted with exogenous amines to form amine bonds.

VI. Dual-Modification of the M13 Bacteriophage

In one particular embodiment, a dual-modified M13 bacteriophage can include both (1) a cancer-targeting substituent covalently attached to the M13 bacteriophage and (2) a fluorescent group covalently attached to the M13 bacteriophage. Such a dual-modified M13 bacteriophage can be utilized to fluorescently tag cancer cells. Specifically, the cancer-targeting substituent (e.g., folic acid) tends to introduce the dual-modified M13 bacteriophage into the cancer cells, effectively tagging the cancer cells with the fluorescent group.

Such a dual-modification can be accomplished using any combination of the above-mentioned modifications of M13 bacteriophage. For example, in one particular embodiment, fluorescent groups can be covalently attached via an amine group (e.g., on an N-terminal amino group of an amino acid or a lysine amino acid of the M13 bacteriophage) and/or via carboxyl groups on the M13 bacteriophage, while the cancer-targeting substituent can be covalently attached via a tyrosine amino acid on the M13 bacteriophage.

EXAMPLES

Example 1

Reactions on Lysine Residues and N-Terminal Amino Groups

By incubating M13 with different concentration of fluorescein-NHS ester or N,N,N',N'-tetramethylrhodamine-NHS (TMRD-NHS) ester, the dye modified M13 was purified by dialysis, precipitation and resuspension in fresh buffer. MALDI-MS analysis of the P8 protein showed the molecular mass of the unmodified M13 subunit was 5,238 m/z (FIG. 2). Small peak at 5,462 m/z could be assigned to the matrix. The mass of the TMRD-HNS modified product indicates that P8 protein can be dual-modified (5,652 m/z and 6,065 m/z). At the similar reaction conditions, fluoroescein-NHS has lower reactivity comparing to TMRD-NHS. The majority of the modified protein subunits are mono-derivatized with rhodamine (5,597 m/z). Small peaks at 5,926 m/z can be assigned to dual-modified protein subunits (FIG. 2). The integrity of the m-M13 was confirmed by both AFM and TEM analysis.

Example 2

Conjugation of Folic Acid on M13

Figure 6:
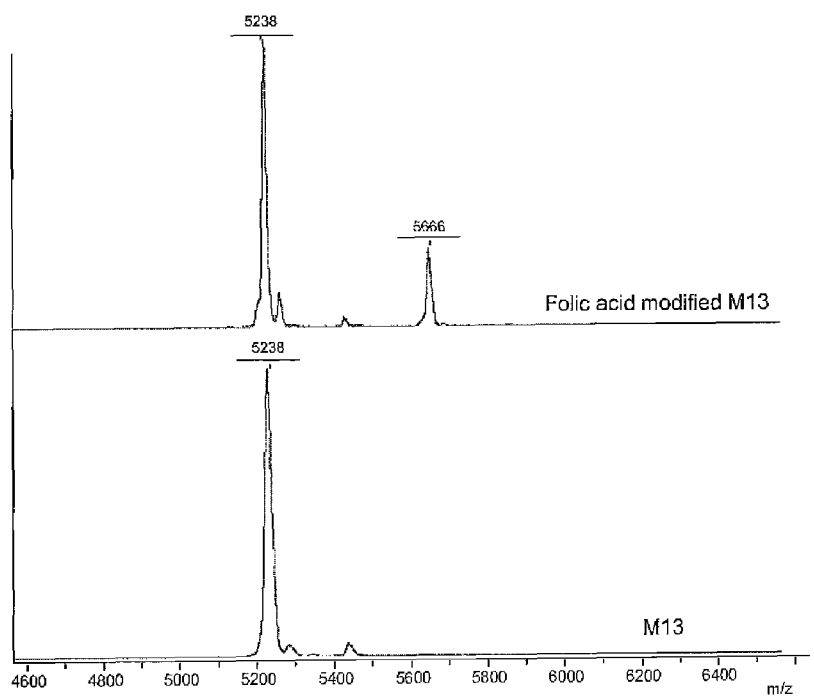
FIG. 6 shows MALDI-TOF MS of the coat protein P8 of unmodified M13 (bottom line) and folic acid modified M13 (top line).

Folic acid which has been exploited as one of the best-characterized ligands for targeting tumor cells, was conjugated onto the surface of M13 bacteriophage by simply incubating M13 bacteriophage, folic acid, EDC and sulfo-NHS at 4° C. for 24 h. MALDI-MS analysis of the P8 protein showed the molecular mass of the unmodified M13 subunit was 5,238 m/z (FIG. 6). The mass of the folic acid modified product indicates that the majority of the modified protein subunits are mono-derivatized with folic acid (5,666 m/z) (FIG. 6). The integrity of the m-M13 was confirmed by both AFM and TEM analysis.

Example 3

Reactivity of Carboxyl Groups

Not like amino residues of P8 coat protein of M13, the carboxyl groups have much lower reactivity. By incubating M13 bacteriophage with fluoresceinamine, EDC and sulfo-NHS in pH 7.8 0.01 M phosphate buffer for 24 h, the fluorescein modified could be readily prepared (FIG. 7). By varying concentration of fluoresceinamine, different amount of dye molecules can be conjugated onto the surface of M13.

Example 4

Reactions on the Tyrosine Residues

The tyrosine residues of M13 bacteriophage are viable for chemical ligation using the electrophilic substitution reaction at the ortho position of the phenol ring with diazonium salts (FIG. 9). A following copper(I)-catalyzed azide-alkyne cycloaddition (CuAAC) reaction can efficiently conjugate many different small molecules such as coumarin, RGD, and other azide substituted compounds onto M13 bacteriophage. For example, a RGD motif can be conjugated to M13 via a two-step approach. M13 was first treated with NHS-alkynes to generate alkynes modified M13. The alkynyl handle has been shown to be a flexible and effective group for the sequential modifications with various functionalities. MALDI-TOF MS analysis indicated that >30% of the protein subunits were decorated with one or two alkyne moieties (alk-M13). A CuAAC reaction was then performed to conjugate RGD-azide to the alkyne groups. The CuAAC reaction was very efficient, and more than 90% of alk-M13 was transferred to RGD modified M13 (RGD-M13).

Example 5

Dual Modification of M13 Bacteriophage with RGD and Rhodamine

Figure 11:
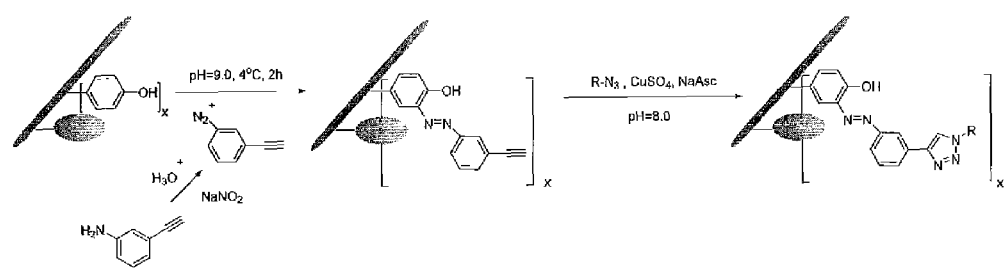
FIG. 11 shows bioconjugation of M13 with TMRD and RGD motifs.
Figure 12:
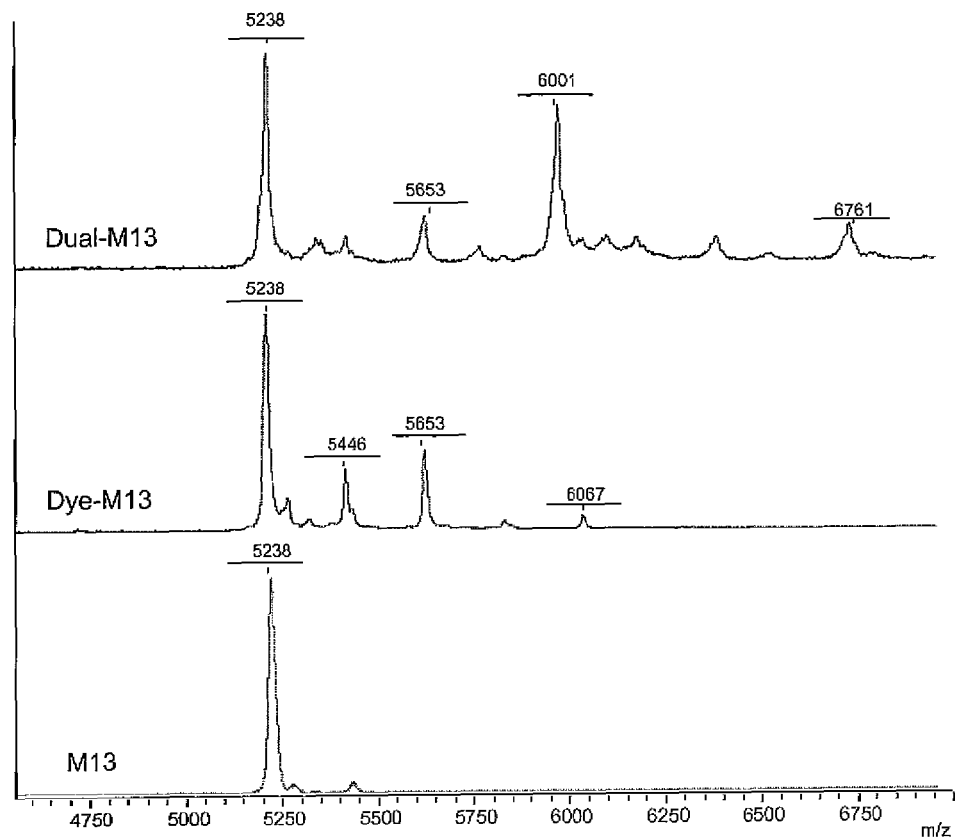
FIG. 12 MALDI-TOF MS of the coat protein P8 of unmodified M13 (5,238 m/z) and modified M13.
Figure 13:
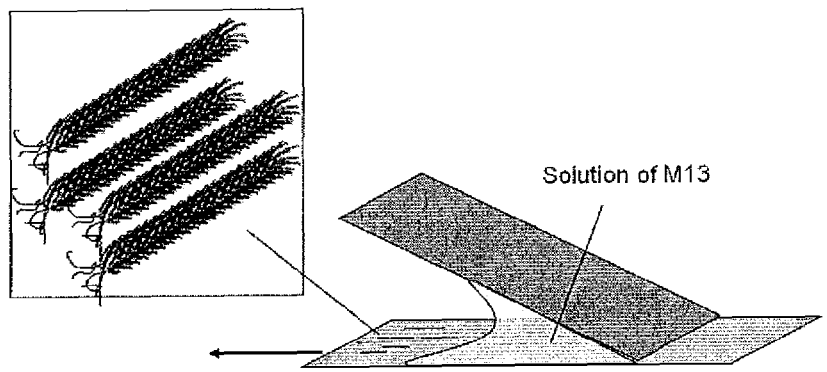
FIG. 13 shows a schematic representation of the system used to deposit aligned bacteriophage.

Combing lysine and tyrosine bioconjugation, the dual-modified M13 bacteriophage could be readily prepared. M13 was first treated with TMRD-NHS to realize florescence dye conjugation. After purification, the dye modified M13 could be further modified with RGD by a two-step tyrosine reaction (FIG. 11). TEM and AFM results showed the dual modified M13 still kept intact after reaction.

It was also demonstrated that the above reactions can also be applied to modified M13 mutants in a similar manner. For example, when a mutant M13, of which pill proteins was genetically altered with avidin binding property, surface modification on pVIII proteins outlined in the previous sections will not interfere with the binding abilities of the pill proteins.

Example 6

Tumor Cell Imaging

Approximately 50,000 cells/well of Hela cells were plated in a 12-well tissue plate containing circular glass cover slips. By incubating Hela cells with 0.2 mg/mL dual modified M13 in the Hela cell culture media at 37° C. in a humidified atmosphere containing 5% CO2. Following desired incubation times, the bacteriophages were removed, and each well was washed with PBS buffer, fixed with 4% paraformaldehyde in PBS and viewed by florescence microscopy. It was clearly seen from the images, after 20 min or 30 min incubation, that most of the dual modified M13 bacteriophages centralize in the Hela cells.

Thus, a new system for tumor cell imaging by conjugating fluorescent dye and RGD onto the surface of M13 bacteriophage has been developed. The dual modified M13 can easily penetrate the cell walls and centralize in the Hela cell. The large dye-carrying capability exhibits highly favorable characteristic for developing M13 bacteriophage as a novel florescence probe for tumor cell targeting and imaging.

Example 7

Fabrication of M13 Thin Film and Directing Cell Growth

Cell behaviors are a complex orchestration of signaling between cell to cell and their surrounding extracellular matrix (ECM). Understanding the biological intricacies between the cell and ECM is critical to general biological questions and the design of functional scaffolds for tissue engineering. Patterning and aligning scaffolds at micro- and nano-scales with topographical features (indentations or grooves) as well as ligand organization have been reported to influence cell responses, in particularly, the oriented cell growth. It was shown here that a new system, the thin film derived from self-assembled bacteriophage M13, can be employed as a new scaffold to direct cell growth. Two techniques were used to generate M13 thin films. One technique is so-called slow drawing. Phage suspension was slowly dried in the well of the 12-well plate over three days to yield liquid crystalline films. Similar to previous reports of M13 viral films, ordered patterns with light and dark band patterns that could be directly visualized under the optical microscope were obtained. The periodic spacing of patterns was from 1 to 4 μm. A mammalian cell line, NIH-3T3 mouse fibroblast, was seeded on the viral films at a density of $1.0 \times 10^4$ cells/cm$^2$. The mouse fibroblasts were maintained in DMEM (HyClone) supplemented with 10% neonatal calf serum, 4 mM L-glutamine, penicillin and streptomycin. NIH-3T3 cells cultured on the viral film exhibited oblong cell bodies, which extended parallel to the band directionality. It was clearly shown that the fibers of the cells were stretched along the long axis of the cells and the nuclei of the cells were also elongated, and aligned to the long axis of the cells. In contrast, NIH-3T3 fibroblasts cells cultured on the non-virus surface showed no preferential elongation or orientation.

Example 8

In order to test the universality of the cell alignment, another mammalian cell, rat aortic smooth muscle cells (RASMCs), a primary cell from rat blood vessel, was cultured on the same viral films. On the M13 aligned film, cells tended to be long and skinny indicative of the contractile morphology. Cells also aligned with the M13 crystal-like thin film. Florescence images show Actin fibers aligned with the M13 surface. Cell density was lower than the cell culture plate. But, florescence imaging of the nuclei showed what was thought of as one cell was actually 3-5 cells forming fibers. This greatly increased the supposed cell number.

Example 9

Scheme 7 illustrates another technique to used to generate the aligned film of M13 on the silane cover glass. Positive charged silane cover glass was used here to offer strong binding between the substrate and M13, which is negatively charged at neutral pH (The isoelectric point for M13 is around 4.4). A solution of bacteriophage M13 (20 mg/mL) was first deposited on glass slide. By slowing dragging the meniscus, the virus solution formed a thin film that exhibited high order of organization of M13 particles. As observed by atomic force microscopy (AFM), the bulk of the M13 bacteriophage is directed towards one uniform direction in large scale. The nanoscale features of the thin film can be observed in the magnified view. RGD modified M13 thin films are composed of a mix of M13 and RGD-M13 bacteriophage solutions at a mass ratio of 3 to 1.

NIH-3T3 fibroblasts cultured on these substrates had elongated and spread on these templates in a single direction. The cells cultured on these films display pronounced extensions. α-Actin fibers were stained with green fluorescent phalloidin to clearly mark the alignment of the cells, which is parallel to the deposition plate withdrawing direction. The addition of RGD modified M13 enhanced cell adhesion and spreading, since the cells cultured on non-modified films do not exhibit the extended cell bodies. Thus by controlling the alignment of M13 particles and surface ligands, thin films with aligned nanofeatures that directs cell outgrowth along a single directionality were generated.

Example 10

In order to test the universality of the cell alignment, another mammalian cell line, Chinese hamster ovarian (CHO) cells, on the same viral films was cultured. The majority of CHO cells formed similar oblong morphologies aligned in a single direction. Both the fibrillar structures and the nuclei of cells were stretched along the long axis of the cells. In contrast, CHO cells cultured on the non-virus surface showed random outgrowth.

CT26.WT, a tumour cell line from mice colon carcinoma was obtained and cultured according to the cell culture protocol. These cells were then seeded at the density of 15K per well in a 12 well plates on aligned M13 thin film in complete growth media. The adhesion, growth and proliferation were monitored every 12 hours. It was observed that the cells grown on the M13 bacteriophage acquires an aligned, elongated spindle shaped morphology compared to the randomly arranged spindle shape on the normal polystyrene cell culture plate.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of modifying a M13 bacteriophage, the method comprising covalently attaching an alkyne functional group to the M13 bacteriophage to form a reactive M13 bacteriophage, wherein the reactive M13 bacteriophage comprises:

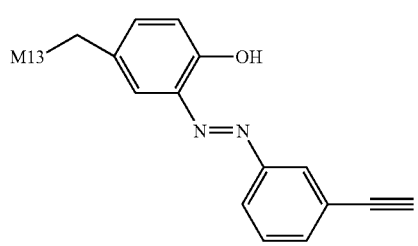

where M13 represents a peptide chain of the M13 bacteriophage; and reacting the alkyne functional group with an azide functional group of a substituent to form a modified M13 bacteriophage covalently bonded to the substituent via a 1,2,3-triazole linkage.

2. The method as in claim 1, wherein the modified M13 bacteriophage covalently bonded to the substituent via the 1,2,3-triazole linkage comprises:

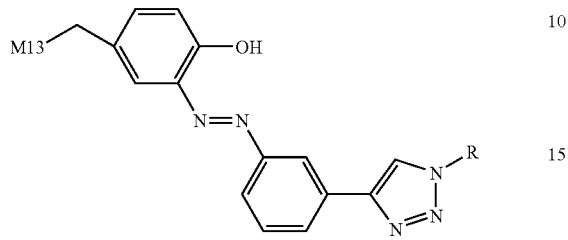

where R represents the substituent and M13 represents a peptide chain of the M13 bacteriophage.

3. The method of claim 1 further comprising
covalently attaching a fluorescent group to the M13 bacteriophage.

4. The method of claim 3, wherein covalently attaching the fluorescent group to the M13 bacteriophage comprises reacting a terminal amine of an alanine amino acid or a functional amino group of a lysine amino acid with the fluorescent group.

* * * * *